United States Patent [19]
Magram

[11] Patent Number: 5,185,778
[45] Date of Patent: Feb. 9, 1993

[54] X-RAY SHIELDING APPARATUS

[76] Inventor: Martin Y. Magram, 3611 Gardenview Rd., Baltimore, Md. 21208

[21] Appl. No.: 744,169

[22] Filed: Aug. 13, 1991

[51] Int. Cl.⁵ .............................................. H05G 1/02
[52] U.S. Cl. .................................. 378/196; 378/209
[58] Field of Search ........................ 378/195, 196, 209

[56] References Cited

U.S. PATENT DOCUMENTS

| | | |
|---|---|---|
| 3,030,508 | 4/1962 | Mort et al. |
| 3,868,103 | 2/1975 | Pageot et al. |
| 4,287,422 | 9/1981 | Kuphal et al. |
| 4,298,801 | 11/1981 | Heitman et al. ............ 378/196 |
| 4,926,456 | 5/1990 | Bock et al. |

*Primary Examiner*—Craig E. Church
*Attorney, Agent, or Firm*—Lowe, Price, LeBlanc & Becker

[57] ABSTRACT

A bar mounted on an operating table on a platform fixedly mounted on a floor carries a switch adapted to be grasped by the hand of a surgeon operating on a patient on the table while x-rays are back-scattered from the table or patient. When the switch is activated to a first state the table is braked. When the switch is activated to a second state, forces manually imparted to an end of the bar by the surgeon are imparted to the table to move the table relative to the platform with the aid of a motor and linkage arrangement. An x-ray shield is interposed between the end of the bar and the table so the body of the operator, including the hand and arm, can be shielded from x-rays back-scattered from the table and/or patient while the hand is grasping the end of the bar and/or the switch. The shield and bar are arranged and dimensioned so that: (1) the operator can stand behind the bar when high intensity cine x-ray radiation is irradiating the patient and (2) the surgeon can stand between the shield and the end of the bar and manipulate an instrument, such as a heart catheterization tool, in proximity to the patient while low intensity fluoroscopy x-ray radiation is irradiating the patient.

17 Claims, 3 Drawing Sheets

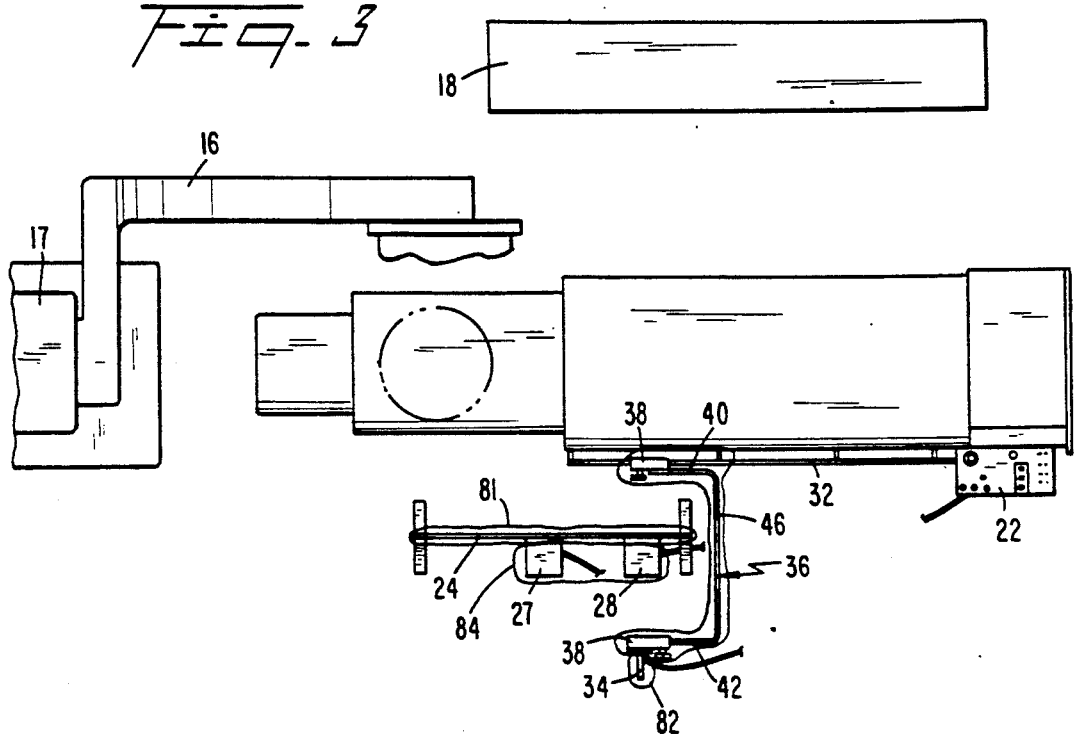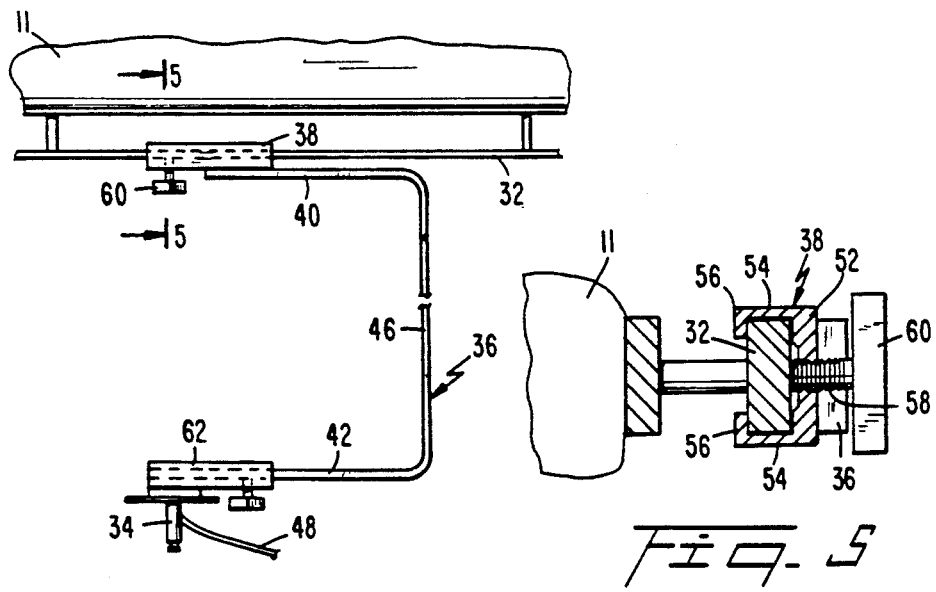

X-RAY SHIELDING APPARATUS

FIELD OF THE INVENTION

The present invention relates generally to x-ray apparatus and more particularly to a bar in combination with a surgical x-ray apparatus, which bar enables the amount of radiation incident on an operator, i.e., a surgeon performing a surgical procedure, to be substantially reduced, because the operator is able to stand behind an x-ray shield and to keep his hand and arm and the remainder of his body behind the shield while imparting manual forces to the table with the bar and selectively activating a switch on the bar which enables the operating table to be moved in response to the manual forces imparted to the bar by the operator.

BACKGROUND ART

In certain surgical procedures, e.g., cardiac catheterization, a patient lying on an operating table carried on a platform fixedly mounted on a floor is irradiated by x-rays for prolonged intervals. During the procedure, the patient is moved relative to a source of the x-rays by providing the table with motors and a linkage that move the table and patient relative to the platform in a plane parallel to the floor. At other times, it is essential that the table and patient remain stationary, a result achieved by providing the table with a braking arrangement for holding the table in situ relative to the platform.

A manually controlled switch is electrically connected to the motor and braking mechanism. When the switch is activated to a first state, during which the surgeon does not press a button of the switch, the table is locked by the brake arrangement. When the switch is activated to a second state, while the surgeon presses the button, the table can be moved as desired by the surgeon, merely by the surgeon pushing or pulling a handle that is fixedly mounted on the table and which carries the button. When the button is pushed, the motor for driving the table is activated so that the surgeon need only exert a minimum amount of force on the handle to move the table to the desired position.

The x-ray source can be activated to different intensity levels. The x-ray source is activated to a high intensity level, referred to as the cine mode, to provide an intensity sufficient to expose cine film and to provide fluoroscopy. The x-ray source is activated to a lower intensity, referred to as the fluoroscopy mode, when only fluoroscopy and no exposure of cine film is required. Typically, there is approximately a 4:1 ratio between the intensity level of the cine and fluoroscopy modes. It is frequently necessary for the surgeon to move the table by exerting forces to the table with the handle during cine mode operation of the x-ray source.

Because the surgeon basically stands next to the operating table, he is constantly exposed to x-rays back-scattered from the patient and/or table. The accumulated effect of the back-scattered radiation over many years of conducting surgical procedures may have deleterious effects on the health of the surgeon, and may induce cancer. In an attempt to reduce the x-ray exposure to a surgeon standing next to the side of an operating table while an x-ray source is irradiating a patient, the surgeon usually wears leaded eyeglasses, a lead thyroid covering and a lead apron which covers the chest, abdomen and thighs but leaves uncovered the arms, hands, legs below the knees and head. The radiation protection is only partially effective in blocking radiation and leaves parts of the body uncovered. Switches to control whether the x-ray source is to be operated in the cine mode or fluoroscopy mode are included in foot control pedals located on the floor. The amount of back-scattered x-ray radiation incident on the surgeon, particularly during the cine mode, is believed to be substantial enough to cause damage to the surgeon over a prolonged time period.

It is, accordingly, an object of the present invention to provide a new and improved structure particularly adapted to reduce the amount of x-rays incident on an operator performing a surgical procedure on a patient who is being irradiated by x-rays during the surgical procedure.

Another object of the present invention is to provide a new and improved structure for enabling a surgeon to keep all of his body parts, including his arm and hand, behind an x-ray shield while performing a surgical procedure during which a patient is irradiated with x-rays and for enabling the surgeon to apply forces to an operating table to move the table relative to a source of the x-rays while activating a button for controlling a motor for enabling the table to be driven by the manual forces.

A further object of the invention is to provide a new and improved method of performing a surgical procedure on a patient lying on an operating table so that the amount of x-ray radiation back-scattered from the patient and the table to the surgeon is substantially reduced, particularly during the cine mode of operating a source of the x-rays.

A further object of the invention is to provide a new and improved method of performing a surgical procedure on a patient lying on an operating table to substantially reduce the amount of x-ray radiation back-scattered to the hand and arm of a surgeon manipulating a handle and a switch which enables a motor to be activated to drive the table in response to forces imparted by the surgeon to the handle.

THE INVENTION

One aspect of the invention is directed to the combination of an operating table mounted on a platform fixedly mounted on a floor and to an x-ray source positioned to irradiate a patient on the table, as well as to motor and brake means for selectively moving the table and holding the table in situ relative to the platform and a manually controlled switch electrically connected to the motor and brake means for selectively controlling movement and locking of the table relative to the platform, and a bar mounted on the table and extending in a direction away from a side of the table where an x-ray shield is positioned. The bar has an end remote from said table side for carrying the switch. The end of the bar is adapted to be grasped by a hand of an operator. The bar is arranged so forces manually imparted to said end by the hand of the operator are imparted to the table to move the table relative to the platform while the switch is in one state. The x-ray shield is disposed between said end of the bar and sites of x-rays back-scattered from the table and/or patient so there is a substantial reduction in exposure of the hand and arm and the remainder of the body of the operator to the back-scattered x-rays while the hand is grasping said bar relative to the exposure of a hand and arm and the remainder of the body of an operator located next to the table without the x-ray shield being disposed.

Each of the x-ray shield and bar is optionally covered with an optically transparent sterile structure, e.g., sterile plastic wrap, if a sterile procedure is being performed. The x-ray shield is approximately three feet wide and six and one-half feet high.

The use of the bar makes the x-ray shield more effective and easier to use. Without the bar, if the operator used a shield, he would need to reach out from behind the shield to grasp the handle attached to the operating table to activate the switch to a second state and move the table. If the operator reached out from behind the shield, he would expose his hand and arm to x-ray radiation and would be in an awkward and uncomfortable position.

In accordance with another aspect of the invention, an apparatus for reducing back-scattered x-rays to a hand and arm and remainder of the body of an operator working with a patient who is exposed to x-rays while on an operating table comprises a switch for controlling a motor and brake means which enables the table to be moved relative to the floor. The switch controls the motor and brake means so that, in response to the switch being activated to a first state, the table is held in situ and, in response to the switch being activated to a second state, the table can be moved in response to forces manually imparted to the table by the operator. A bar is mounted on the table and extends in a direction away from a side of the table. The bar has an end remote from said side of the table for carrying the switch. The end of the bar remote from the side of the table is adapted to be grasped by the hand of an operator. The bar is dimensioned and arranged so (a) forces manually imparted to said end by the hand of the operator are imparted to the table to move the table relative to the platform while the switch is in the second state, and (b) an x-ray shield can be interposed between said end of the bar and sites of the back-scattered x-rays so exposure of the hand and arm and remainder of the body of the operator to the back-scattered x-rays while the operator is grasping said one end is substantially reduced relative to the exposure of a hand and arm and remainder of the body of an operator located next to the table without the x-ray shield being interposed. In the preferred embodiment, a portion of the bar including said end of the bar extends generally parallel to said side of the table and the bar is arranged and dimensioned so that the operator can stand behind said portion of the bar relative to said side of the table or between said portion of the bar and said shield when the shield extends generally parallel to said side of the table.

To enable the surgeon to stand behind the bar or in front of the bar, with the shield disposed between his body and the table, the bar has a length of approximately 30 inches in a direction away from said side of the table.

In accordance with a further aspect of the invention, a surgical procedure is performed on a patient lying on an operating table mounted on a platform fixedly attached to a floor. Motor and brake means enable the table to be moved relative to the platform and floor in response to manually imparted forces while a switch is activated to a second state. The motor and brake means also prevents movement of the table while the switch is activated to a first state. The switch is on an end of a bar fixedly attached to a side of the table. Said end of the bar is on a portion of the bar generally extending parallel to said side of the table. An x-ray shield extending generally parallel to said side is interposed between said side of the table and said portion of the bar. The method comprises activating an x-ray source that is irradiating the patient to a fluoroscopy mode while an operator is standing between the shield and the bar portion and is performing the procedure on the patient with his hand and arm extending beyond the shield in proximity to the patient and the switch is activated to the first state since it is not engaged by the operator. The amount of exposure to the hand and arm of the operator is relatively low while the x-ray source is activated to the fluoroscopy mode and therefore the hand and arm of the operator are not subjected to a great deal of x-ray radiation. The x-ray source is activated to irradiate the patient to a cine mode while the operator is standing behind the bar portion and the shield with his hands and arms behind the shield. The operator activates the switch to the second state at this time and imparts manual forces to the bar to move the table while he stands behind the bar with his hands and arms behind the shield.

Another feature of the invention relates to the combination of an operating table mounted on a platform fixedly mounted on a floor and to an x-ray source positioned to irradiate a patient on the table, as well as to motor and brake means for selectively moving the table and holding the table in situ relative to the platform and a manually controlled switch electrically connected to the motor and brake means for selectively controlling movement and locking of the table relative to the platform. The x-ray shield is mounted for movement relative to the table (preferably by casters) and includes foot pedal switch means for controlling the intensity of x-rays emitted by the source. In the preferred embodiment, the foot pedal switch means includes first and second foot pedal switches for respectively activating the x-ray source into the cine and fluoroscopy modes.

BRIEF DESCRIPTION OF THE DRAWING

FIG. 3 is a top view of an operating table and x-ray facility incorporating the present invention.

FIG. 4 is a detailed view of the side of an operating table and a preferred embodiment of the invention;

FIG. 5 is a detailed view, taken through the lines 5—5, of a structure for holding a bar in accordance with the present invention on an operating table track.

DESCRIPTION OF THE PREFERRED EMBODIMENT

The preferred embodiment of the present invention is described in conjunction with a cardiac catheterization procedure. It is to be understood, however, that the principles of the invention are applicable to any surgical or radiological procedure wherein a patient is subject to x-ray radiation for prolonged time periods and an operator attending to the patient, i.e., a surgeon or radiologist, is subject to x-rays back-scattered from the patient and/or operating table on which the patient is lying.

Figure 1:
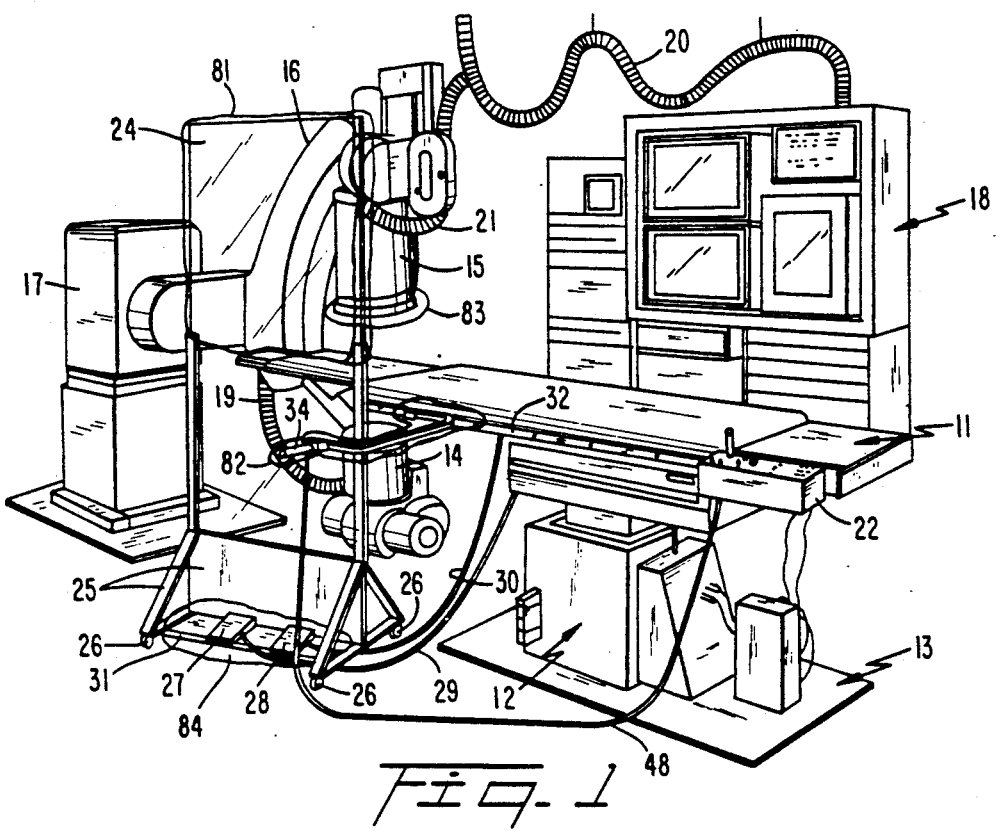
FIG. 1 is a perspective drawing of an operating table and x-ray facility incorporating the present invention.
Figure 2:
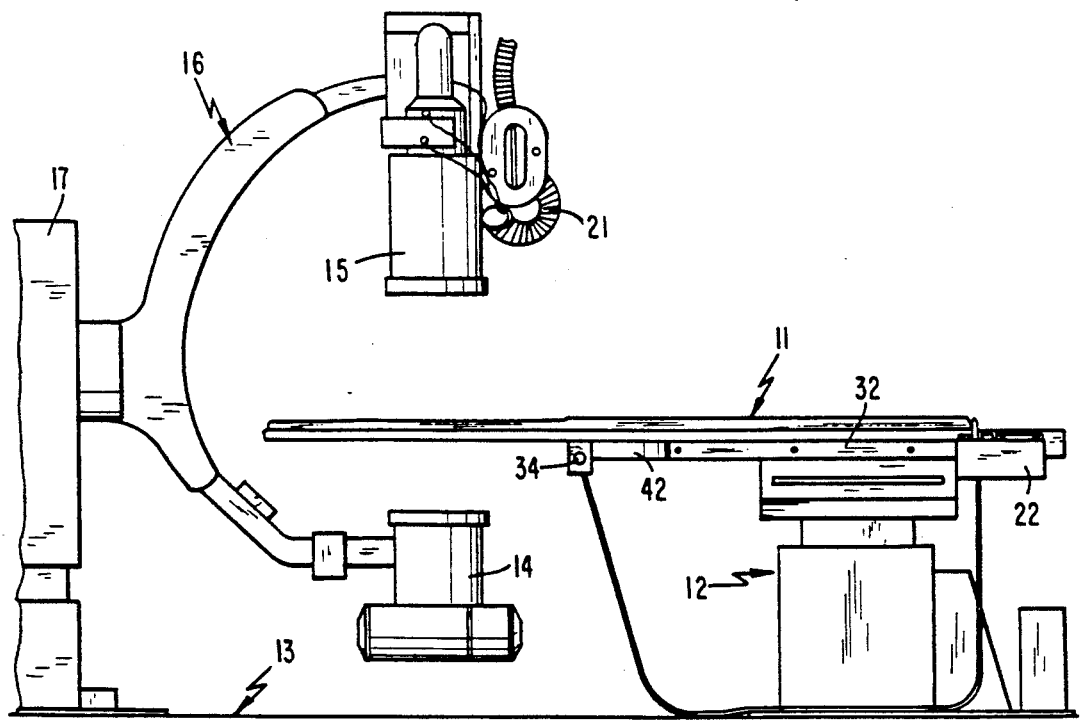
FIG. 2 is a side view of an operating table and x-ray facility incorporating the present invention.

Reference is now made to FIGS. 1–3 of the drawing wherein operating table 11 is mounted on platform 12, which in turn is fixedly mounted on floor 13 so that the operating table extends in a horizontal plane parallel to the floor. Platform 12 includes X-Y linkages (not shown) and motors, as well as a braking mechanism, as well known to those skilled in the art. The linkages and motors enable forces manually applied by the surgeon to the table to move the table in the horizontal plane, even though a relatively heavy patient is lying on table 11. The linkages and motor in platform 12 are controlled, as described infra, by the surgeon selectively activating a button, so that when the button is pushed, the manually-imparted forces cause table 11 to move in the horizontal plane. When the button is not activated, the linkages and the motors in platform 12 are braked by the braking mechanism in the platform to prevent movement of table 11 relative to platform 12 and the floor 13.

X-ray source 14 and x-ray detector 15, in the form of an image intensifier, are mounted on gantry 16 so that the tube and detector are mounted on opposite sides of table 11 and the patient lying on the table. Gantry 16 is mounted for rotation on column 17, located on floor 13. Circuitry in x-ray source 14 and image-intensifier 15 is controlled by power and signals coupled to them from an x-ray controller (not shown) via cable 19. The x-ray image is transmitted via cable 20 from an x-ray controller (not shown) through the ceiling to video display 18. Power for the cine recorder is provided by cable 21. Typically, x-ray source 14 is activated to one of two different intensity levels, respectively referred to as the fluoroscopy and cine modes, such that the cine mode has an intensity level four times greater than that of the fluoroscopy mode. Control console 22 for the movement of table 11 as well as for x-ray source 14 is fixedly mounted on one end of operating table 11.

In a typical operating room, lead impregnated plastic, optically transparent vertically extending x-ray shield panel 24 is located in proximity to one side of table 11. Shield panel 24 is mounted on bracing structure 25, on which are mounted casters 26 for enabling the shield panel to be easily moved relative to platform 12 on floor 13. Shield panel 24 extends from about a foot above floor 13 to about 6½ feet above the floor and for about 3 feet from side to side so the entire body of a surgeon standing behind the panel is effectively shielded from x-rays back-scattered from table 11 and the patient lying on the table. Shield panel 24 includes, at the bottom portion thereof (just above casters 26), platform 31 on which are carried foot pedal switches 27 and 28. Switches 27 and 28 are respectively connected by cables 29 and 30 to the x-ray controller (not shown) to control the intensity of the x-rays generated by tube 14. In response to foot pedal switches 27 and 28 being respectively activated, the x-ray controller (not shown) activates source 14 to cause the fluoroscopy and cine intensity levels to be derived from the source. The surgeon stands behind panel 24, i.e., on the side of the panel remote from table 11, during cardiac catheterization procedures and steps on one of foot pedal switches 27 or 28 to control the x-ray intensity level.

In the prior art, if a shield panel is used the physician must reach out from behind shield panel 24 and grasp a handle selectively fixedly mounted to track 32, in turn fixedly mounted to extend along one side of table 11. The surgeon imparts a force to the handle, hence track 32 and table 11, while activating one of foot pedal switches 27 or 28 and the switch on the handle to move the patient and table 11 relative to x-ray source 14 and image intensifier 15. While the low intensity fluoroscopy x-rays are irradiating the patient as a result of foot pedal switch 27 being activated, the physician stands in front or to the side of panel 24 while holding a cardiac catheterization tool in one or both of his hands. Thereby, during the fluoroscopy mode, the entire body of the physician is subjected to x-rays back-scattered from the patient and table and the physician receives no benefit from the shielding properties of panel 24. During the higher intensity cine mode operation, the physician frequently stands to one side of panel 24 and holds the handle mounted on track 32, while selectively activating the control button for the linkages and motors in platform 12, to enable table 11 and the patient lying on the table to be moved relative to x-ray source 14 and detector 15. Hence, during the cine operation, while the surgeon is pressing foot pedal 28, one arm and hand of the surgeon are irradiated by x-ray radiation back-scattered from the patient and table 11. Over a prolonged period of many years, the surgeon is, therefore, subjected to considerable amounts of x-ray radiation back-scattered from the table and patients on which he has performed the cardiac catheterization procedure. The accumulated effects of the back-scattered radiation on the surgeon may lead to the surgeon becoming a cancer victim.

In accordance with the present invention, the entire body of the surgeon is shielded from x-ray radiation during the cine mode of operation of x-ray tube 14. This result is achieved by fixedly mounting handle 34, which carries push button 37 (FIG. 6) for control of the linkages and motor in platform 12, on U-shaped bar 36, fixed to track 32 by block 38. U-shaped bar 36 includes legs 40 and 42 that extend generally parallel to track 32 and the side of table 11 on which track 32 is mounted, as well as base 46, having a length of approximately 30 inches. Base 46 extends at right angles to track 32 so that panel 24 can be positioned behind leg 40 while the surgeon stands between panel 24 and leg 42.

During the fluoroscopy mode, after panel 24 has been moved close to leg 40, the physician stands behind shield panel 24 while one of his feet engages switch pedal 27 and his right arm and hand extend around the right edge (as illustrated) of shield panel 24. In this position the surgeon holds the catheterization tool with his right hand in close proximity to the body of the patient.

Prior to initiating the cine mode of operation, panel 24 is moved away from table 11, into proximity with leg 42 of bar 36. The surgeon next positions his entire body behind shield panel 24 and grasps handle 34 with his right hand and selectively activates foot pedal switch 28 and control button 37. Because the entire body of the physician is behind shield panel 24 and his position is farther away from table 11 and the patient, the entire body of the physician is shielded from the x-rays back-scattered from the patient and the table. Forces are manually imparted by the physician to the table while control button 37 is activated and foot pedal switch 28 is activated to enable the patient to be moved relative to x-ray source 14. Because the intensity of the radiation is a function of the inverse square of the distance between the source of the radiation and the subject being irradiated, the intensity of the x-ray radiation back-scattered from table 11 and the patient that is incident on the physician is considerably reduced during the cine mode of operation c npared to the prior art. A further reduction in radiation intensity occurs because shield panel 24 is interposed between virtually the entire body (except the lower portion of the legs) of the physician and sites of the back-scattered x-rays. The U-shape of bar 36 and the length of the bar enable access to the patient from behind panel 24 with one step. Hence, the particular size and shape of bar 36 enable convenient operation of the equipment, while providing protection to the surgeon.

The present invention is frequently used during sterile operating room procedures. If sterile procedures are used, panel or shield 24, handle 34 and bar 36, and x-ray detector 15 are respectively enclosed in optically transparent and sterile wrappings 81, 82 and 83, preferably made of sterile plastic wrap. Foot pedal switches 27 and 28 are enclosed in plastic wrap 84 which seals them from dripping patient body fluids, to prevent short-circuiting of contacts in the foot pedal switches.

Details of structures for holding bar 36 in situ on track 32 and for mounting handle 34 and the circuitry associated therewith are illustrated in FIGS. 5-8. As illustrated in FIG. 5, block 38 includes base 52 and legs 54 from which extend flanges 56, arranged to fit snugly on side walls and edges of track 32. To hold bar 36 in situ on block 38, two screws are used (not shown). To position block 38 on track 32, threaded shaft 58 of thumb screw 60 extends through a bore in block 38; the thumb screw is threaded until the end of shaft 58 engages the side wall of track 32.

Figure 6:
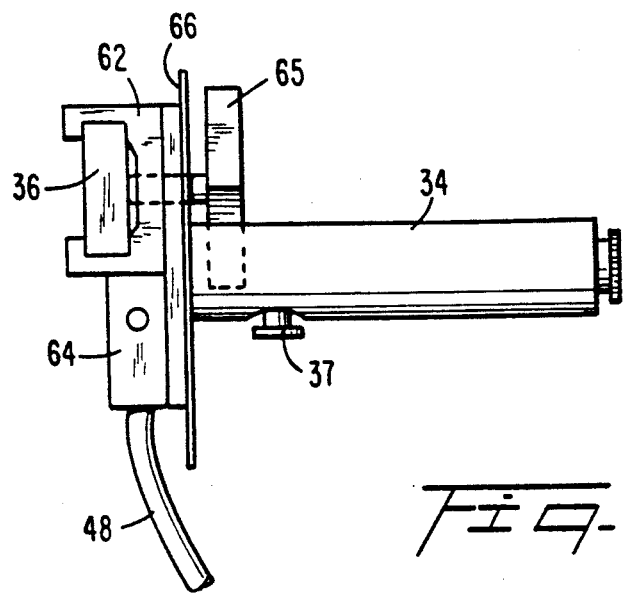
FIGS. 6-8 are respectively detailed side, front and back views of an end of a bar in accordance with the present invention, in combination with a handle and a switch.
Figure 7:
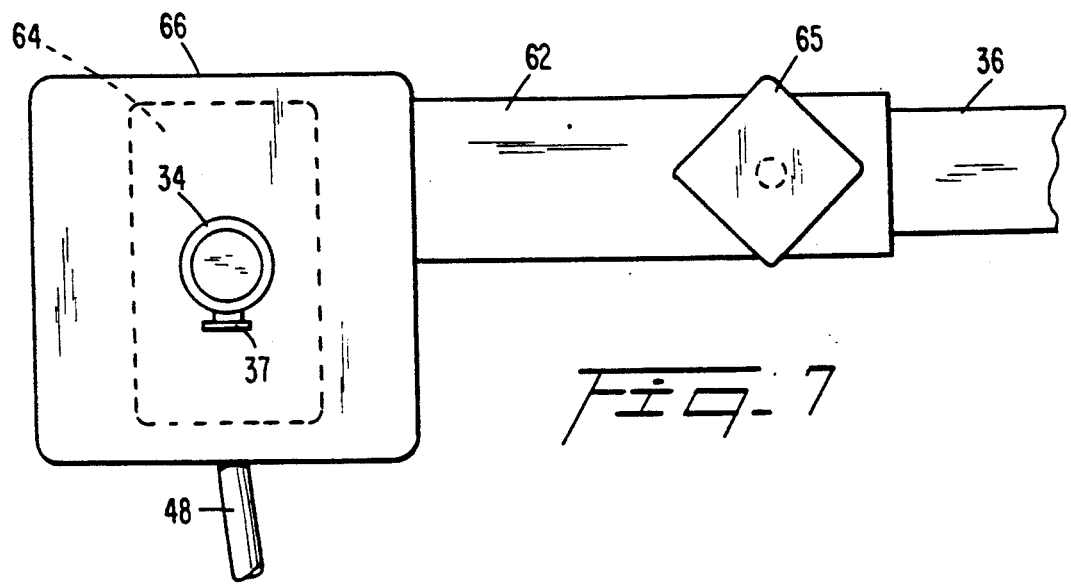
Figure 8:
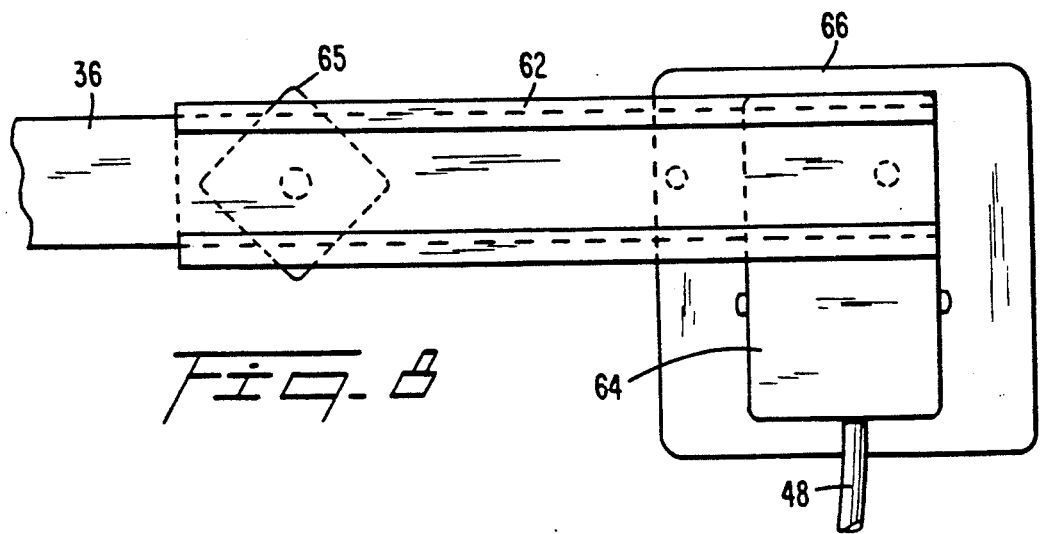

As illustrated in FIGS. 6-8, at the other end of bar 36 is block 62 on which are mounted handle 34 and housing 64 for the switch contacts controlled by button 37. Block 62 is constructed similarly to block 38 and is held in situ by thumb screw 65 in the same manner that block 38 is secured to track 32. Block 62 includes a bore for receiving the threaded shaft of turn screw 65. Housing 64 is secured to plate 66. Housing 64 is fixedly mounted to block 62. A mechanical linkage is coupled between push button 37 and the switch contacts in housing 64 to close the contacts when the button is pushed. Closure of the contacts causes a signal to be transmitted from housing 64 to control console 22 via cable 48. The switch contacts are normally spring biased to the open state so that upon release of button the contacts open.

While there has been described and illustrated one specific embodiment of the invention, it will be clear that variations in the details of the embodiment specifically illustrated and described may be made without departing from the true spirit and scope of the invention as defined in the appended claims.

I claim:

1. In combination, an operating table mounted on a platform fixedly mounted on a floor, an x-ray source positioned to irradiate a patient on the table, x-rays from the source when incident on the table or a patient on the table being back-scattered away from the table, motor and brake means for selectively moving the table and holding the table in situ relative to the platform, a manually controlled switch electrically connected to the motor and brake means for selectively controlling movement and locking of the table relative to the platform, an x-ray shield positioned on a side of the table, a bar mounted on the table and extending in a direction away from the side of the table, the bar having an end remote from the table side for carrying the switch and adapted to be grasped by the hand of an operator, the bar being arranged so forces manually imparted to said end by the hand of the operator are imparted to the table to move the table relative to the platform, the x-ray shield being interposed between said end of the bar and sites of the back-scattered x-rays so exposure of the operator to the back-scattered x-rays while the hand is grasping said end is substantially reduced relative to the exposure of an operator located next to the table without the x-ray shield being interposed.

2. The combination of claim 1 wherein said shield and a portion of said bar including said end of the bar extend generally parallel to said side of the table and the bar is arranged and dimensioned so that the operator can stand behind said portion of the bar relative to said side of the table or between said portion of the bar and said shield.

3. The combination of claim 1 wherein the x-ray shield is mounted for movement relative to the table and carries a foot pedal switch means for controlling the intensity of x-rays emitted by the source.

4. The combination of claim 3 wherein the x-ray shield includes casters.

5. The combination of claim 3 wherein the bar, shield and manually activated switch means are enclosed in an optically transparent, sterile wrap means.

6. The combination of claim 3 wherein the foot pedal switch is located behind a fluid impervious shield so dripping patient body fluids are not incident on contacts of the foot pedal switch.

7. The combination of claim 1 wherein the bar, shield and manually activated switch means are enclosed in an optically transparent, sterile wrap means.

8. Apparatus for reducing back-scattered x-rays incident on a hand and arm of an operator working with a patient on an operating table, the patient being exposed to x-rays while on the table, the table being mounted on a platform fixedly mounted on a floor, the table being selectively moved relative to the floor by motor and brake means, the apparatus comprising a switch for controlling the motor and brake means so that in response to the switch being activated to a first state the table is held in situ and in response to the switch being activated to a second state the table can be moved in response to forces manually imparted to the table, a bar mounted on the table and extending in a direction away from a side of the table, the bar having an end remote from said side for carrying the switch and adapted to be grasped by the hand of an operator, the bar being dimensioned and arranged so (a) forces manually imparted to said end by the hand of the operator are imparted to the table to move the table relative to the platform while the switch is in the second state, and (b) an x-ray shield can be interposed between said end of the bar and sites of the back-scattered x-rays so exposure of the operator to the back-scattered x-rays while the operator is grasping said one end is substantially reduced relative to the exposure of an operator located next to the table without the x-ray shield being interposed.

9. The apparatus of claim 8 wherein said shield and a portion of said bar including said end of the bar extend generally parallel to said side of the table and the bar is arranged and dimensioned so that the operator can stand behind said portion of the bar relative to said side of the table or between said portion of the bar and said shield when the shield extends generally parallel to said side of the table.

10. A method of performing a surgical procedure on a patient lying on an operating table mounted on a platform fixedly attached to a floor, motor and brake means for enabling the table to be moved relative to the platform in response to manually imparted forces while a switch is activated to a second state and for preventing movement of the table while the switch is activated to a first state, the switch being on an end of a bar fixedly attached to a side of the table, said end of the bar being on a portion of the bar generally extending parallel to said side, an x-ray shield extending generally parallel to said side being interposed between said side of the table and said portion of the bar, the method comprising: activating an x-ray source irradiating the patient to a fluoroscopy mode while an operator is standing between the shield and the bar portion and is performing the procedure on the patient with his hand extending beyond the shield in proximity to the patient and the switch is activated to the first state, and activating the x-ray source irradiating the patient to a cine mode while the operator is standing behind the bar portion and shield with his hand and arm behind the shield, the operator activating the switch to the second state and imparting manual forces to the bar to move the table while he stands behind the bar with his hand and arm behind the shield.

11. The method of claim 10 wherein the x-ray source is activated to the cine mode while the operator is activating the switch to the second state and imparting manual forces to the bar to move the table.

12. In combination, an operating table mounted on a platform fixedly mounted on a floor, an x-ray source positioned to irradiate a patient on the table, x-rays from the source when incident on the table or a patient on the table being back-scattered away from the table, motor and brake means for selectively moving the table and holding the table in situ relative to the platform, a switch manually controlled by an operator, said switch being electrically connected to the motor and brake means for selectively controlling movement and locking of the table relative to the platform while the switch is respectively in first and second states, an x-ray shield positioned on a side of the table, means responsive to operations by the operator for controlling movement of the table relative to the platform while the switch is in the first state, said last named means having an operator control site, the x-ray shield being interposed between the manually controlled switch and the operator control site and sites of the back-scattered x-rays so exposure of the operator to the back-scattered x-rays while the operator is operating said manually controlled switch and is at the operator control site is substantially reduced relative to the exposure of an operator located next to the table without the x-ray shield being interposed.

13. The combination of claim 12 wherein the x-ray shield is mounted for movement relative to the table and carries a foot pedal switch means for controlling the intensity of x-rays emitted by the source.

14. The combination of claim 13 wherein the x-ray shield includes casters.

15. The combination of claim 13 wherein the foot pedal switch is located behind a fluid impervious shield so dripping patient body fluids are not incident on contacts of the foot pedal switch.

16. A method of performing a surgical procedure by an operator on a patient lying on an operating table mounted on a platform fixedly attached to a floor, motor and brake means for enabling the table to be moved relative to the platform in response to imparted forces while a switch is activated by the operator to a second state and for preventing movement of the table while the switch is activated by the operator to a first state, an actuator responsive to the operator for controlling movement of the table, an x-ray shield extending generally parallel to said side being interposed between said side of the table and a site for said actuator, the method comprising:

activating an x-ray source irradiating the patient to a fluoroscopy mode while the operator is standing behind the shield and is performing the procedure on the patient with his hand extending beyond the shield in proximity to the patient and the operator is activating the switch to the first state, and activating the x-ray source irradiating the patient to a cine mode while the operator is standing behind the shield with his hand and arm behind the shield, the operator activating the switch to the second state and activating the actuator to move the table while he stands behind the bar with his hand and arm behind the shield.

17. The method of claim 16 wherein the x-ray source is activated to the cine mode while the operator is activating the switch to the second state and activating the actuator to move the table.

* * * * *